United States Patent [19]

Kato

[11] 4,198,431
[45] Apr. 15, 1980

[54] ALKYL N-(3-TRIFLUOROMETHYLPHENYL)-ANTHRANILATE

[75] Inventor: Hideo Kato, Katsuyamashi, Japan

[73] Assignee: Hokuriku Pharmaceutical Co., Ltd., Japan

[21] Appl. No.: 874,494

[22] Filed: Feb. 2, 1978

[51] Int. Cl.² .................. A61K 31/245; C07C 101/54
[52] U.S. Cl. ....................................... 424/310; 560/47
[58] Field of Search .................. 560/47; 424/309, 310

[56] References Cited

U.S. PATENT DOCUMENTS

| 3,144,387 | 8/1964  | Jones ................ 260/518     |
| 3,413,339 | 11/1968 | Scherrer ............. 560/47      |
| 3,558,690 | 1/1971  | Sallmann et al. ...... 560/47      |
| 3,767,811 | 10/1973 | Sherlock ............. 424/310     |
| 3,855,230 | 12/1974 | Water et al. ......... 424/310     |
| 4,029,815 | 6/1977  | Sherlock et al. ...... 560/47      |
| 4,143,151 | 3/1979  | Wagner et al. ........ 424/310     |

FOREIGN PATENT DOCUMENTS 2948M 9/1963 France ....................... 560/48
44-94352 11/1969 Japan.

OTHER PUBLICATIONS

Klebanov et al., Chem. Absts., vol. 82, 363p (1975).
Salimbeni et al., Chem. Absts., vol. 83, 274f (1975).
Manghisi et al., Chem. Absts., vol. 77, 114067(x) 1972).

*Primary Examiner*—Joseph E. Evans
*Assistant Examiner*—G. T. Breitenstein
*Attorney, Agent, or Firm*—Gordon W. Hueschen

[57] ABSTRACT

N-(3-trifluoromethylphenyl)anthranilic acid esters represented by the formula (I):

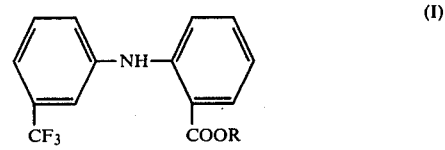

wherein R represents an alkyl group having 4 to 8 carbon atoms, are disclosed.

The esters are useful as anti-inflammatory agents, particularly for an external application, with reduced toxicity. These esters are of great importance as non-steroid type anti-inflammatory agents for topical administration.

14 Claims, No Drawings

ALKYL N-(3-TRIFLUOROMETHYLPHENYL)-ANTHRANILATE

BACKGROUND OF THE INVENTION

1. Field of the Invention

The present invention relates to an N-3-trifluoromethylphenyl)anthranilic acid ester represented by the formula (I):

$$\text{CF}_3\text{-C}_6\text{H}_4\text{-NH-C}_6\text{H}_4\text{-COOR} \quad (I)$$

wherein R represents an alkyl group having 4 to 8 carbon atoms, inclusive.

2. Description of the Prior Art

French Patent M 2948 discloses the corresponding methyl and ethyl esters. However, these esters are not satisfactory since they provide relatively high toxicity. Further, U.S. Pat. No. 3,144,387 discloses N-(3-trifluoromethylphenyl)anthranilic acid per se as an anti-inflammatory agent which is orally administered.

SUMMARY OF THE INVENTION

Accordingly, a primary object of the present invention is to provide novel esters of N-(3-trifluoromethylphenyl)anthranilic acid, having excellent anti-inflammatory activity, and pharmaceutical compositions embodying the same.

Further objects of the present invention are to provide specific esters of N-(3-trifluoromethylphenyl)anthranilic acid having reduced toxicity, particularly suitable for an external application, such as in the form of ointments, due to their quality of excellent absorption by the skin, and a method of treating inflammation therewith.

DETAILED DESCRIPTION OF THE INVENTION

According to the present invention, novel alkyl esters of N-(3-trifluoromethylphenyl)anthranilic acid are provided. Preferred are alkyl esters having 4 to 8 carbon atoms. Specific examples of such esters include butyl, iso-butyl, sec-butyl, tert-butyl, n-pentyl, iso-pentyl, tert-pentyl, n-hexyl, n-heptyl, n-octyl, etc. Of these esters, most preferred is the n-butyl ester or N-(3-trifluoromethylphenyl)anthranilic acid.

The compounds represented by the formula (I) can be prepared by conventional methods. For brevity, reference is specifically made to the compound represented by the formula (I) wherein R is a butyl group.

(i) Following a conventional method for esterification of an acid, either (a) n-butanol is reacted with N-(3-trifluoromethylphenyl)anthranilic acid, an acid anhydride thereof or a halide thereof, or (b) an n-butyl halide is reacted with an alkali metal salt (e.g., a sodium salt or potassium salt) of the acid, the butyl ester thereby being obtained.

The esterification can proceed at normal room temperatures (about 25° C.) or by heating at about 80° to about 150° C. in a solvent in the presence of a dehydrating agent or an acid-binding agent. Any solvent can be employed as long as it does not prevent the esterification. Typical examples of these solvents are n-butanol, benzene, toluene, xylene, dimethyl formamide, pyridine, etc. Suitable examples of dehydrating agents which are preferably employed in the esterification include conc. sulfuric acid, phosphorour oxychloride, p-toluene sulfonic acid, etc. Preferred examples of acid-binding agents are tertiary amines, anhydrous potassium carbonate, anhydrous sodium carbonate, pyridine, etc.

(ii) The compound represented by the formula (I) can also be prepared by reacting m-trifluoromethyl aniline and an n-butyl o-halogeno benzoate in the presence of a copper catalyst, in which the halogen is Cl, Br, I or F.

The reaction proceeds by heating at about 100° to about 200° C. without any solvent or in a solvent in the presence of a copper catalyst (e.g., copper powders, cupric oxide, etc.). In order to eliminate the hydrohalogenic acid released during the reaction, an acid-binding agent (potassium carbonate, etc.) is employed. Suitable examples of solvents are dimethyl formamide, dimethyl sulfoxide, etc.

The compounds represented by the formula (I) are nonsteroid type anti-inflammatory agents showing excellent anti-inflammatory activity. What is particularly notable with repsect to these anti-inflammatory agents is that they exhibit far less toxicity while still maintaining anti-inflammatory activity comparable to conventional anti-inflammatory agents which are presently available on the market. For instance, side-by-side comparison has established that the compounds of the present invention possess a strong edema-preventing effect at two and three hours after external administration which is approximately 1.5 times that produced by the compound Bufexamac (generic name, made by Nippon Lederle Co., Ltd.), represented by the formula:

$$CH_3CH_2CH_2CH_2O\text{-}C_6H_4\text{-}CH_2CONHOH$$

Bufexamac the details of which are described in Belgian Pat. No. 661,226.

The compounds of the present invention can be administered orally or parenterally. Parenteral administration of the compounds, and especially topical administration, is particularly advantageous and preferred.

Again, their most advantageous and surprising effect is their remarkably low level of toxicity. By the simple expedient of modifying the esters from a methyl or ethyl ester to a higher alkyl ester, the $LD_{50}$ of the compounds of the present invention is reduced to about one-half that of the corresponding methyl or ehtyl ester.

Using ddY type male mice, acute toxicity ($LD_{50}$) was examined after oral administration of the methyl, ethyl and butyl esters, respectively.

The results are shown in the table which follows:

Table 1

| Compound | $LD_{50}$ (95% Confidence Limit) (mg/kg) |
| --- | --- |
| I | 1625 (1448–1823) |
| II | 1825 (1589–2100) |
| Compound of Invention | 3100 (2262–4249) |

Test Compounds:

I: Methyl N-(3-trifluoromethylphenyl)anthranilate
II: Ethyl N-(3-trifluoromethylphenyl)anthranilate

Compound of Invention:

n-Butyl N-(3-trifluoromethylphenyl)anthranilate

As can be clearly seen from the data shown in the table, the $LD_{50}$ of the compound of this invention is only about one-half ($\frac{1}{2}$) as much as the $LD_{50}$ of the corresponding methyl ester or ethyl ester. In a similar manner, $LD_{50}$ was examined with regard to the $C_5$–$C_8$ higher alkyl esters. A tendency that the toxicity was more reduced with the increased carbon atom number was observed, e.g., about 5000 mg/kg in the $LD_{50}$ of the n-octyl ester.

Next, the carrageenin edema-preventing effect [E. Yamazaki, et al., *Folia Pharmacologica Japonica*, vol. 63, page 302 (1967)] was examined using an ointment containing a five-percent(5%) concentration of active ingredient.

Experiment:

Using ten (10) Wistar female rats as one grouping, each test compound was applied at the rate of fifty (50) mg/rat onto the sole of the rear paws thrity (30) minutes. After carrageenin was subcutaneously administered (1% carrageenin: 0.1 ml/rat) at the ointment-administered area, the volume was measured over a period of five (5) hours, during which a definite amount (50 mg/rat) of each test compound was administered every hour over a period of four (4) hours after the first measurement of the paw volume. The edema-preventing effect was thus determined in contrast to known compounds. In Table 2 following, the swelling percent (rate of volume increase) is given. The figures in parenthesis indicate the rate of edema prevention which was calculated in contrast to control. In control, carrageenin alone was administered.

The results are shown in Table 2 following.

Table 2

| Compound | Time (hr.) | | | | |
|---|---|---|---|---|---|
| | 1 | 2 | 3 | 4 | 5 |
| Control | 37.1% | 74.4% | 83.9% | 83.3% | 80.8% |
| N-(3-trifluoromethyl-phenyl)anthranilic acid | 28.4% | 61.8% | 62.3% | 61.4% | 61.2% |
| (preventing rate) | (23.5) | (16.9) | (25.8) | (26.3) | (24.2) |
| Compound of Invention* | 23.5% | 47.3% | 54.8% | 55.5% | 50.0% |
| (preventing rate) | (36.7) | (36.4) | (34.7) | (33.4) | (38.1) |

*n-Butyl N-(3-trifluoromethylphenyl)anthranilate

As can be clearly seen from the results shown in the foregoing Table 2, the compound in accordance with the present invention exhibits improved edema-preventing effect as compared to the known compound. This is believed to be because the compound of the present invention is more effectively absorbed through the skin than the known acid.

The butyl ester of the invention and Bufexamac were further compared in ointment form with respect to the edema-preventing effect thereof.

Experiment:

Using eight (8) Wistar male rats, weighing 120 to 140 g., as one grouping, 50 mg. each of the test ointments was applied onto the sole of rear paws 3, 2 and 1 hours before an agent which induced inflammation was administered, after the paw volume at one side was measured. Carrageenin (1%: 0.1 ml.) was subcutaneously administered as the inflammation-inducing agent. Thereafter, the paw volume was again measured every hour over a period of five (5) hours. An edema-preventing rate was determined from the volume prior to administration of the inflammation-inducing agent.

The results are shown in Table 3.

Table 3

| Compound | Time (hr.) | | | | |
|---|---|---|---|---|---|
| | 1 | 2 | 3 | 4 | 5 |
| Control | 48% | 90% | 95% | 91% | 88% |
| Ointment Base | 43% | 85% | 89% | 84% | 78% |
| Compound of Invention* | 43% | 63%*** | 68%** | 69% | 68% |
| (preventing rate) | (10.4) | (30.0) | (28.4) | (24.2) | (22.7) |
| Bufexamac | 43% | 73% | 76% | 76% | 72% |
| (preventing rate) | (10.4) | (18.9) | (18.9) | (16.5) | (17.2) |

*n-Butyl N-(3-trifluoromethylphenyl)anthranilate
**p 0.05
***p 0.02

The present invention will be explained in more detail with reference to the following examples, but is not to be considered limited thereto.

EXAMPLE 1 n-Butyl N-(3-trifluoromethylphenyl)anthranilate:

In anhydrous dimethyl formamide was dissolved 3.2 g. of potassium salt of N-(3-trifluoromethylphenyl)anthranilic acid. To the solution was added 5.0 g. of n-butyl bromide. The mixture was heated at 100°–120° C. for 5 hrs. while stirring. The precipitated potassium bromide was taken out by filtration. The filtrate was concentrated and the residue obtained was distilled to obtain 3.1 g. of light yellow liquid having a boiling point of 190°–192° C. (5 mmHg).

IR Spectra (cm$^{-1}$):
3300 (NH), 1685 (—COO—)

Mass Spectra (m/e): 337(M$^+$). 281, 263 (base peak)

EXAMPLE 2

A mixture of 3.0 g. of N-(3-trifluoromethylphenyl)anthranilic acid, 23 ml. of n-butanol and 0.3 ml. of conc. sulfuric acid was stirred to reflux for 24 hrs. The excess n-butanol was removed by distillation under reduced pressure. Water was added to the residue, which was rendered alkaline by adding an aqueous solution of sodium hydroxide. The alkaline solution was extracted with n-hexane. The n-hexane layer was washed with water and dried. The solvent was removed by distillation. n-Hexane was again added to the resulting residue, followed by treatment with active charcoal. The residue obtained by distilling the solvent off was distilled to obtain 3.3 g. of light yellow liquid having a boiling point of 169°–170° C. (1 mmHg).

The analytical data of the product were identical with those of the compound obtained in accordance with Example 1.

EXAMPLE 3

A mixture of 21.25 g. of m-aminobenzotrifluoride, 5.0 g. of n-butyl o-iodobenzoate, 3.0 g. of anhydrous potassium carbonate and 0.2 g. of cupric oxide was heated to 140°–160° C. and stirred for 6 hrs. After the completion of the reaction, the reaction mixture was filtered. The filtered substances were washed with ether. Water was added to the filtrate. The aqueous layer was extracted with ether. The ethereal layer was washed with water and dried. After evaporating the solvent off, the residue was distilled to obtain 1.73 g. of light yellow liquid, showing a boiling point of 169°–170° C. (1 mmHg). The analytical data of the product were identical with those of the compound obtained in accordance with Examples 1 and 2.

In a similar manner, the following compounds were obtained.

$$\underset{CF_3}{\bigcirc}-NH-\underset{COOR}{\bigcirc}$$

| Example | R | Boiling Point and Melting Point Mass Spectra (m/e) |
|---|---|---|
| 4 | iso-butyl | b.p. 152°–154° C. (1.5 mmHg) 337(M+), 281, 263 |
| 5 | sec-butyl | b.p. 147°–148° C. (1 mmHg) 337(M+), 281, 263 |
| 6 | tert-butyl | m.p. 60°–61° C. 337(M+), 281, 263 |
| 7 | n-pentyl | b.p. 170°–171° C. (1 mmHg) 351(M+), 281, 263 |
| 8 | iso-pentyl | b.p. 168°–169° C. (2 mmHg) 351(M+), 281, 263 |
| 9 | tert-pentyl | b.p. 162°–164° C. (1 mmHg) 351(M+), 281, 263 |
| 10 | n-hexyl | b.p. 177°–178° C. (1 mmHg) 365(M+), 281, 263 |
| 11 | n-heptyl | b.p. 172°–175° C. (1 mmHg) 379(M+), 281, 263 |
| 12 | n-octyl | b.p. 187°–188° C. (1 mmHg) 379(M+), 281, 263 |

In tests of the same nature and comparable to those set forth in the foregoing, the additional foregoing Compounds 4 through 12 of the present invention exhibit the enhanced anti-inflammatory activity and reduced toxicity in the same manner as the n-butyl compound.

The high order of anti-inflammatory activity of the active agents of the present invention, together with their reduced toxicity, is evidenced by tests in lower animals, representative of which are reported herein. These new compounds of the invention can be administered per os, e.g., in the form of pills or tablets, in which they are present together with the usual pharmaceutical carriers, excipients, binders, and the like. Tablets may be prepared conventionally by compounding one of the new compounds together with a customary carrier or adjuvant, such as talc, magnesium stearate, starch, lactose, gelatin, any of numerous gums, and the like. Thus, in their most advantageous form, the compositions of the invention will contain a non-toxic pharmaceutical carrier in addition to the active anti-inflammatory ingredient of the present invention. Exemplary solid carriers are lactose, magnesium stearate, calcium stearate, starch, terra alba, dicalcium phosphate, sucrose, talc, stearic acid, gelatin, agar, pectin, acacia, or the like. Representative liquid carriers are peanut oil, sesame oil, olive oil, water, or the like. The active agents of the invention can be conveniently administered in such compositions containing about 1.0 to about 50%, preferably 10 to 50% for oral administration and 1.0 to 10% for topical administration, by weight of active ingredient. Thus, a wide variety of pharmaceutical forms suitable for many modes of administration and dosages may be employed. For oral administration, the active ingredient and pharmaceutical carrier may, for example, take the form of a granule, pill, tablet, lozenge, elixir, syrup, or other liquid suspension or emulsion whereas, for topical administration, the usual liquid suspension or emulsion, powders, creams, salves, and especially such compositions of the nature of an ointment, may be employed, with the ointment compositions being preferred.

The method of using the compounds of the present invention comprises internally or topically administering compounds of the invention, preferably admixed with the pharmaceutical carrier, for example, in the form of any of the above-mentioned compositions, or filled into a capsule, to alleviate inflammatory conditions and symptoms thereof in a living animal body. Illustratively, they may be employed in an amount of about 10 to about 500 milligrams per unit dose, preferably about 100 to about 500 milligrams for an oral dose, usually about 200 milligrams, while topical dosages are usually less and ordinarily about 10 to about 100 milligrams, preferably about 50 milligrams. The unit dose is preferably given a suitable number of times daily, typically two or three times so that the daily dose may vary depending upon the number of times. For many purposes, a suitable clinical dose may be between 10 and 500 mg. Naturally, the dosabe must be adjusted in accord with the condition, age, and weight of the patient, and it goes without saying that the enhanced anti-inflammatory activity of the compounds of the invention, together with their reduced toxicity, also makes them suitable for veterinary applications. The compounds are obviously subject to wide variations in optimum daily and unit dosages, due to patient body weight, conditions, and ancillary factors, and the invention therefore should not be limited by the exact ranges stated. The exact dosage, both unit dosage and daily dosage, will of course have to be determined according to established medical and/or veterinary principles. In addition, the active ingredients of the present invention or compositions containing the same may either be administered concurrently with or include other physiologically active materials and/or medicaments, such as buffering agents, antacids, sedatives, stimulants, anticholi nergics, analgesics, neuroleptics, minor tranquilizers, or the like. For purposes of the method-of-treating aspects of the present invention, it is of course only necessary that an effective anti-inflammatory dose of a compound of the present invention be administered to the living animal body or host in need of such anti-inflammatory therapy, whether this be by the oral route or by parenteral route, and preferably by the topical route, especially in the form of an ointment.

A suitable tablet formulation may be as set forth in U.S. Pat. No. 4,021,564 and, or course, as previously stated, the anti-inflammatory active compounds provided by the present invention may also be administered successfully by embodying an effective anti-inflammatory quantity thereof in oral powders, suspensions, or syrups, or in other acceptable dosage forms.

Although as previously stated very small quantities of the active materials of the present invention are effective when minor therapy is involved or in cases of administration to subjects having a relatively low body weight, unit dosages are usually within the range set forth above, or even higher, depending of course upon the emergency of the situation and the particular results desired. To repeat, the exact individual dosages as well as daily dosages in a particular case will of course be determined according to established medical principles under the supervision of the physician or veterinarian involved in treatment of the particular inflammatory syndrome which is being treated. In general, due to their lower toxicity and higher degree of anti-inflammatory activity, the compounds of the present invention may be administered in compositions and in amounts which are the same as, somewhat below or somewhat above, the amounts currently employed for the anti-inflammatory product known generically as Bufexamac. Again, balancing the anti-inflammatory activity and toxicity in combination, the butyl ester is most preferred as a non-steriod type anti-inflammatory agent in accordance with the present invention.

While the invention has been described in detail and with reference to specific embodiments thereof, it will be apparent to one skilled in the art that various changes and modifications can be made therein without departing from the spirit and scope thereof.

What is claimed is:

1. An N-(3-trifluoromethylphenyl)anthranilic acid ester represented by the formula:

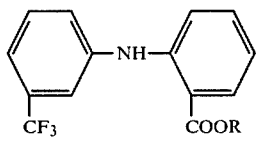

wherein R represents an alkyl group having 4 to 8 carbon atoms, inclusive.

2. The anthranilic acid ester as claimed in claim 1 wherein R is n-butyl.
3. The anthranilic acid ester as claimed in claim 1 wherein R is iso-butyl.
4. The anthranilic acid ester as claimed in claim 1 wherein R is sec-butyl.
5. The anthranilic acid ester as claimed in claim 1 wherein R is tert-butyl.
6. The anthranilic acid ester as claimed in claim 1 wherein R is n-pentyl, iso-pentyl or tert-pentyl.
7. The anthranilic acid ester as claimed in claim 1 wherein R is n-hexyl.
8. The anthranilic acid ester as claimed in claim 1 wherein R is n-heptyl.
9. The anthranilic acid ester as claimed in claim 1 wherein R is n-octyl.
10. A pharmaceutical composition, useful as an anti-inflammatory agent, containing an effective anti-inflammatory amount of an N-(3-trifluoromethylphenyl)anthranilic acid ester represented by the formula:

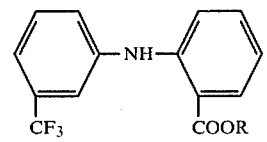

wherein R represents an alkyl group having 4 to 8 carbon atoms, inclusive, together with a pharmaceutically acceptable carrier.
11. The pharmaceutical composition of claim 10, in the form of a topical pharmaceutical suitable for external application.
12. The pharmaceutical composition as claimed in claim 11 wherein said anthranilic acid ester is n-butyl ester.
13. A method for the treatment of a patient suffering from inflammation, comprising the step of topically administering to said patient a compound of claim 1 in an amount effective for alleviation of said condition.
14. The method of claim 13, wherein the compound administered is the n-butyl ester of N-(3-trifluoromethylphenyl)anthranilic acid and wherein the compound is administered topically.

* * * * *

UNITED STATES PATENT AND TRADEMARK OFFICE
CERTIFICATE OF CORRECTION

PATENT NO. : 4,198,431
DATED : April 15, 1980
INVENTOR(S) : Hideo Kato

It is certified that error appears in the above—identified patent and that said Letters Patent is hereby corrected as shown below:

Col. 2, line 5; "phosphorour" should read -- phosphorous --
Col. 2, line 25; "repsect" should read -- respect --
Col. 3, line 26; "thrity" should read -- thirty --
Col. 6, line 36; "dosabe" should read -- dosage --
Col. 7, line 26; "steriod" should read -- steroid --
Col. 8, line 33; "pharmaceutical suitable" should read -- pharmaceutical composition suitable --

Signed and Sealed this

Eleventh Day of November 1980

[SEAL]

Attest:

Attesting Officer

SIDNEY A. DIAMOND

Commissioner of Patents and Trademarks